United States Patent [19]

Dogimont et al.

[11] Patent Number: 5,146,013
[45] Date of Patent: Sep. 8, 1992

[54] PROCESS FOR THE PRODUCTION OF CHLOROFORM FROM CARBON TETRACHLORIDE, CATALYTIC COMPOSITIONS AND PROCESS FOR OBTAINING THEM

[75] Inventors: Charles Dogimont; James Franklin, both of Brussels; Francine Janssens, Vilvoorde; Jean-Paul Schoebrechts, Grez-Doiceau, all of Belgium

[73] Assignee: Solvay & Cie (Société Anonyme), Brussels, Belgium

[21] Appl. No.: 669,618

[22] Filed: Mar. 14, 1991

[30] Foreign Application Priority Data

Nov. 16, 1990 [BE] Belgium .............................. 09001086

[51] Int. Cl.$^5$ .............................................. C07C 17/00
[52] U.S. Cl. .................................................... 570/101
[58] Field of Search ................................. 570/101, 176

[56] References Cited

U.S. PATENT DOCUMENTS 3,579,596  5/1971  Mullin et al. ......................... 570/101

FOREIGN PATENT DOCUMENTS 1578933  11/1980  United Kingdom ................ 570/176

*Primary Examiner*—Alan Siegel
*Attorney, Agent, or Firm*—Spencer, Frank & Schneider

[57] ABSTRACT

The invention relates to a process for the production of chloroform from carbon tetrachloride using a catalytic composition comprising a support on which a hydrogenating metal is deposited, the support comprising an alkali metal aluminate or alkaline earth metal aluminate.

The invention also relates to a catalytic composition comprising a support on which platinum is deposited, the support comprising an aluminate having an inverse spinel structure.

15 Claims, No Drawings

PROCESS FOR THE PRODUCTION OF CHLOROFORM FROM CARBON TETRACHLORIDE, CATALYTIC COMPOSITIONS AND PROCESS FOR OBTAINING THEM

The invention relates to a process for the production of chloroform from carbon tetrachloride using a catalytic composition. The invention also relates to particular catalytic compositions allowing such a process and to a process for obtaining these catalytic compositions.

U.S. Pat. No. 3,579,596 discloses, in particular, processes for the dechlorination of carbon tetrachloride to chloroform in the gas phase in the presence of a catalyst chosen from the metals Ru, Rh, Pd, Os, Ir, Pt, Cu, Ag or Au and the support of which is formed by alumina, active charcoal or silica.

However, the processes known to date are accompanied by secondary reactions and/or a rapid deactivation of the catalysts, which jeopardises the efficacy of these processes.

The invention, by contrast, relates to a process for the production of chloroform from carbon tetrachloride which no longer has these disadvantages. In fact, it has been found that some catalytic compositions permit a dechlorination of carbon tetrachloride with a selectivity or a degree of conversion, that is to say a yield, which have never been achieved previously, and more particularly the process according to the invention makes it possible to obtain, using carbon tetrachloride as the starting material, chloroform and methane virtually exclusively, and, moreover, with a reduced formation of $C_2$ compounds.

Moreover, these employed catalytic compositions have the main advantage of being more stable and of deactivating much more slowly than the known catalytic compositions.

To this end, the invention relates to a process for the production of chloroform from carbon tetrachloride, in the gas phase in the presence of molecular hydrogen, in which process the reaction is catalysed by a catalytic composition comprising at least one metal having a hydrogenating character deposited on a support comprising at least one alkali metal aluminate or alkaline earth metal aluminate.

A metal having a hydrogenating character is understood to be metals of group VIII and of group IB of the periodic table of the elements. Customarily, the hydrogenating metal is chosen from the metals Ru, Rh, Pd, Os, Ir, Pt, Cu, Ag or Au. Preferably, the hydrogenating metal is platinum or palladium. Good results have been obtained with platinum.

A support comprising at least one alkali metal aluminate or alkaline earth metal aluminate is understood to be all catalytic supports comprising at least one or more aluminates of one or more alkali metals or of one or more alkaline earth metals. In general, the catalytic support comprises at least one alkali metal aluminate. Customarily, the catalytic support comprises a lithium aluminate, magnesium aluminate or calcium aluminate. Preferably, the support comprises an aluminate having a mixed oxide structure. Very preferentially, the support comprises an aluminate having an inverse spinel structure. Particularly preferably, the support comprises lithium aluminate of formula $LiAl_5O_8$. Very particularly preferentially, the support comprises lithium aluminate of formula $LiAl_5O_8$ and the oxide $LiAlO_2$. Good results have been obtained with a catalytic composition in which the support consists to at least 75% of aluminate $LiAl_5O_8$.

The catalytic support may also comprise a mixed aluminate or a mixture of at least two different aluminates of one or more metals selected from alkali metals and alkaline earth metals. Good results have been obtained with a catalytic composition in which the support consists of a mixed aluminate of lithium and sodium.

In general, from 0.01 to 5% by weight of metal having a hydrogenating character is used. These percents are based on the weight of the catalytic composition support. Preferably, from 0.05 to 1.0% by weight is used.

The process according to the invention takes place in the gas phase.

The temperature at which the reaction takes place is customarily between 50° and 200° C. Preferably, this temperature is between 80° and 170° C. Good results have been obtained for the selective production of chloroform from carbon tetrachloride using a reaction temperature of between 90° and 150° C.

The pressure at which the reaction takes place is generally between 0.1 and 10 ats. Preferably, it is between 1 and 8 ats. Good results have been obtained with a pressure of between 1 and 6 ats.

The molar ratio between hydrogen and carbon tetrachloride which is employed is generally between 1 and 16. Preferably, this ratio is between 4 and 14. Good results have been obtained with a ratio of between 6 and 12. Molar ratios located within this region promote the selectivity for chloroform; moreover, dilution of the gas phase slows down the formation of carbon deposits on the catalytic composition.

In the same sense, the gas phase is also advantageously diluted by methane, which slows down the ageing of the catalytic composition. Thus, the process according to the invention may be carried out in the presence of methane. In general, the molar ratio between methane and carbon tetrachloride which is employed is between 0.1 and 15. Preferably, this ratio is between 3 and 12. Good results have been obtained with a ratio of between 4 and 10.

The average contact time, that is to say the ratio between the volume of the part of the reactor occupied by the catalyst and the flow rate of the reactants at the reaction pressure and reaction temperature is generally between 1 and 30 s. Customarily it is between 2 and 15 s. Good results have been obtained with a contact time of between 4 and 10 s.

The process according to the invention is carried out using a catalytic composition arranged in a fixed bed or in a fluidised bed.

The process according to the invention is carried out in any equipment or reactor enabling the reaction conditions described to be combined.

The invention also relates to particular catalytic compositions for the production of chloroform form carbon tetrachloride.

The invention relates to catalytic compositions comprising a support comprising at least one aluminate having an inverse spinel structure, on which at least platinum is deposited, as metal having a hydrogenating character.

The support of the catalytic compositions according to the invention comprises at least one aluminate having an inverse spinel structure. Preferably, the support comprises lithium aluminate of formula $LiAl_5O_8$. Particularly preferentially, the support comprises lithium aluminate of formula $LiAl_5O_8$ and the oxide $LiAlO_2$. Good results have been obtained with a catalytic composition in which the support consists to at least 75% of aluminate $LiAl_5O_8$.

The support of the catalytic compositions may also comprise a mixed aluminate or a mixture of at least two different aluminates of one or more metals selected from alkali metals and alkaline earth metals. Good results have been obtained with a catalytic composition in which the support consists of a lithium-sodium mixed aluminate.

The catalytic compositions according to the invention generally comprise from 0.01 to 5% by weight of platinum relative to the weight of the catalytic composition support. Preferably, they comprise from 0.05 to 1.0% by weight of platinum relative to the weight of the catalytic composition support.

The specific surface area of the catalytic compositions according to the invention is generally between 15 and 60 m$^2$/g and preferably between 20 and 50 m$^2$/g.

The pre volume of the catalytic compositions according to the invention is generally between 0.1 and 0.8 cm$^3$/g and preferably between 0.3 and 0.5 cm$^3$/g.

When lithium aluminate is the only aluminate in the support, the Li/Al ratio in the catalytic compositions according to the invention is generally between $\frac{1}{4}$ and 1/5.5 and is preferably about 1/5.

The catalytic compositions may be obtained by any process known in this field.

Customarily, the process for the preparation of these catalytic compositions comprises three steps:
  the preparation of the support,
  the impregnation of this support with a hydrogenating metal compound, such as a platinum compound, and
  the activation of the catalytic composition.

One method for obtaining the support comprised in the catalytic compositions according to the invention which has given good results consists in bringing into contact an alumina and a solution of an alkali metal compound or alkaline earth metal compound capable of forming an oxide, removing the water and then subjecting the product obtained to a calcination heat cycle which converts the alkali metal compound or alkaline earth metal compound to a corresponding oxide and gives rise to the reaction between the alumina and the alkali metal oxides or alkaline earth metal oxides. Excellent results have been obtained when a gamma-alumina is brought into contact with a lithium compound which is a precursor of the oxide, such as a nitrate or an acetate.

For the preparation of the catalytic composition, the preparation of the support is followed by the impregnation of the support with a hydrogenating metal compound, such as a platinum compound. A preparation which has given good results consists in bringing the support into contact with an acid solution of a platinum compound under vacuum. Preferably, the reaction is carried out in the presence of chloroplatinic acid hexahydrate dissolved in hydrochloric acid.

Before use, the catalytic composition is activated. An activation which has given good results consists in flushing the catalytic composition successively:
  under air or under oxygen at a temperature of between about 100° and 150° C.,
  then under air or under oxygen at a temperature of between about 500° and 550° C.,
  under an inert gas such as nitrogen, at a temperature of between 75° and 125° C.,
  under hydrogen, at a temperature of between 250° and 300° C. and
  finally under an inert gas such as nitrogen at ambient temperature.

After use of the catalytic compositions of the invention, the catalytic composition may be regenerated without significant loss of activity and selectivity. A regeneration process which has given good results consists in applying two (flushing) treatments with air at about 350° C. for a period of 24 hours to the catalytic composition, each treatment being followed by a reduction under hydrogen at about 280° C. for 8 hours. Another process consists in a regeneration under hydrogen at a temperature of between 200° and 350° C.

The invention is illustrated more fully by the following examples.

EXAMPLE 1

Preparation of the Catalytic Composition a) Preparation of the Support 16.4 g of $LiOH.H_2O$ and 28 ml of concentrated $HNO_3$ are introduced into a conical flask. Water is added to the solution obtained so as to obtain a total volume of 35 ml.

Alumina (gamma-alumina having a specific surface area of 303 m$^2$/g and a pore volume of 0.35 cm$^3$/g) is dried at 100° C. under vacuum.

100 g of alumina thus dried are then impregnated at ambient temperature and at atmospheric pressure with the solution obtained above.

The mixture is allowed to stand for one hour at ambient temperature.

The product thus obtained is dried under vacuum at 90° C. for 45 minutes.

The support obtained is then calcined under air by stages of 6 hours at 600° C. and 8 hours at 1050° C.

b) Impregnation 5 g of chloroplatinic acid hexahydrate are dissolved in 100 ml of a 0.05 M hydrochloric acid solution.

4.5 ml of this solution are taken and diluted with 4.8 ml of water.

17.1 g of the support obtained as described in paragraph a) are placed for 2 hours under vacuum at 100° C. in a 500 ml grooved flask. The temperature is then allowed to return to ambient temperature under vacuum. The solution prepared above is then added to this support in the course of 75 minutes and under vacuum at ambient temperature.

The composition obtained is allowed to stand at ambient temperature and at atmospheric pressure for 24 hours.

The composition is placed in a vacuum oven at 100° C. for 72 hours.

c) Activation

The composition obtained as described in paragraph b) is placed in a reactor for calcination, which is flushed with air at 130° C. for 4 hours.

The reactor is then brought to 530° C. for 1 hour under air.

The reactor is then cooled under nitrogen to 100° C. and left to stand overnight under these conditions.

The reactor is then brought to 280° C. under nitrogen and is then flushed with hydrogen for 8 hours at 280° C.

The reactor is brought back to ambient temperature while flushing with nitrogen.

The Li/Al ratio of the catalytic composition is 1/5. X-ray diffraction analysis of the catalytic composition after grinding indicates the presence of three phases, the predominant constituent of which is $LiAl_5O_8$.

The specific surface area and the pore volume of the catalytic composition determined by adsorption of nitrogen are, respectively, 33 $m^2/g$ and 0.37 $cm^3/g$.

EXAMPLE 2

Production of Chloroform from Carbon Tetrachloride

10 $cm^3$ (7.65 g) of the catalytic composition obtained as described in Example 1 are introduced as a fixed bed into a stainless steel reactor having an internal diameter of 10.2 mm and heated by means of a pulsed-air oven.

The reactor is fed with a gas mixture consisting of 82.8% by volume of hydrogen and 17.2% by volume of carbon tetrachloride at a temperature of 105° C. under a pressure of 4.3 bar and at a space velocity (that is to say the inverse of the average contact time) of 480 $h^{-1}$, which corresponds to a hydrogen flow rate of 12.3 1N/h and a carbon tetrachloride flow rate of 2.56 1N/h.

The initial degree of conversion of carbon tetrachloride is 95 mol %.

The products formed are chloroform, dichloromethane, methane, hydrochloric acid and traces of ethane and perchloroethylene. The selectivities, based on carbon tetrachloride converted, are, respectively, 75 mol % for chloroform, 2 mol % for dichloromethane and 22 mol % for methane.

After passing through 152 kg of carbon tetrachloride/g of platinum, that is to say after about 330 hours of operation, the degree of conversion of carbon tetrachloride is still 81 mol %; the selectivities for the products formed are unchanged.

EXAMPLE 3

Production of Chloroform from Carbon Tetrachloride—Dilution of the Carbon Tetrachloride with Hydrogen After the reactor containing the catalytic composition of Example 1 has been in operation for 330 hours under the conditions of Example 2, a gas mixture consisting of 89.4% by volume of hydrogen and 10.6% by volume of carbon tetrachloride is introduced into the reactor at a temperature of 105° C. under a pressure of 4 bar and at a space velocity of 480 $h^{-1}$, which corresponds to hydrogen and carbon tetrachloride flow rates of, respectively, 12.40 and 1.47 1N/h.

Under these conditions the degree of conversion of carbon tetrachloride is 84 mol %. The selectivities, based on carbon tetrachloride converted, are, respectively, 84 mol % for chloroform, 0.7 mol % for dichloromethane and 15 mol % for methane.

After passing through a further 39 kg of carbon tetrachloride per g of platinum, that is to say after about 145 hours' additional operation, the degree of conversion of carbon tetrachloride is 82 mol %; the selectivities for the products formed remain unchanged.

EXAMPLE 4

Long Duration Test

30 $cm^3$ (24 g) of the catalytic composition obtained in Example 1 are mixed with 20 $cm^3$ of glass beads and this mixture is introduced as a fixed bed into a stainless steel reactor having an internal diameter of 20 mm, which is heated by means of circulating oil in a double wall.

A gas mixture consisting of 44.4% by volume of hydrogen, 44.4% by volume of methane and 11.2% by volume of carbon tetrachloride is passed through the catalytic composition at a temperature of 102° C., under a pressure of 4.0 bar and at a space velocity of 514 $h^{-1}$ (relative to the non-diluted catalytic composition), which corresponds to hydrogen, methane and carbon tetrachloride flow rates of, respectively, 20.0, 20.0 and 5.0 1N/h.

The degree of conversion of carbon tetrachloride is 98 mol %. The main products formed are chloroform, dichloromethane, methane and hydrochloric acid. The selectivities, based on carbon tetrachloride converted, are, respectively, 83 mol % for chloroform, 1 mol % for dichloromethane and 16 mol % for methane.

After passing through 270 kg of carbon tetrachloride per g of platinum (about 940 hours of operation), the degree of conversion of carbon tetrachloride and the selectivities for the products formed remain unchanged.

EXAMPLE 5R

Comparative

10 $cm^3$ (4.99 g) of a catalytic composition containing 0.5% of platinum deposited on a theta-alumina are introduced as a fixed bed into a stainless stell reactor having an internal diameter of 10.2 mm, which is heated by means of a pulsed air oven.

The reactor is fed with a gas mixture consisting of 83.1% by volume of hydrogen and 16.9% by volume of carbon tetrachloride at a temperature of 90° C., under a pressure of 4.04 bar and at a space velocity of 514 $h^{-1}$, which corresponds to a hydrogen flow rate of 12.98 1N/h and a carbon tetrachloride flow rate of 2.65 1N/h.

The degree of conversion of carbon tetrachloride is 90 mol %.

The main products formed are chloroform, dichloromethane, methane, hydrochloric acid, perchloroethylene and hexachloroethane. The selectivities, based on carbon tetrachloride converted, are, respectively, 67 mol % for chloroform, 4 mol % for dichloromethane, 23 mol % for methane, 5 mol % for perchloroethylene and 0.5 mol % for hexachloroethane.

After passing through 17 kg of carbon tetrachloride/g of platinum, that is to say after about 24 hours of operation, the degree of conversion of carbon tetrachloride is still 66 mol %; the selectivities, based on carbon tetrachloride converted are, respectively, 72 mol % for chloroform, 0 mol % for dichloromethane, 23 mol % for methane, 3 mol % for perchloroethylene and 2 mol % for hexachloroethane.

EXAMPLE 6

Preparation of the Catalytic Composition a) Preparation of the Support 8.2 g of $LiOH.H_2O$, 14 ml of concentrated $HNO_3$ and 16.62 g of $NaNO_3$ are introduced into a conical flask. Water is added to the solution obtained so as to obtain a total volume of 44 ml.

Alumina (gamma-alumina having a specific area of 300 $m^2/g$ and a pore volume of 0.4 $cm^3/g$) is dried at 100° C. under vacuum.

100 g of alumina thus dried are then impregnated at ambient temperature and at atmospheric pressure with the solution obtained above.

The mixture is allowed to stand for one hour at ambient temperature.

The product thus obtained is dried under vacuum at 90° C. for 45 minutes.

The support obtained is then calcined under air by stages for 6 hours at 600° C. and 8 hours at 1050° C.

The global formula of the support is $(Li,Na)_1Al_5O_8$.

b) Impregnation 5 g of chloroplatinic acid hexahydrate are dissolved in 100 ml of a 0.05 M hydrochloric acid solution.

26.5 ml of this solution are taken and diluted with 17.5 ml of water.

100 g of the support obtained as described in paragraph a) are placed for 45 minutes under vacuum at 90° C. in a 500 ml grooved flask. The temperature is then allowed to return to ambient temperature under vacuum. The solution prepared above is then added to this support in the course of 80 minutes and under vacuum at ambient temperature.

The composition obtained is then placed in a vacuum oven at 100° C. for 24 hours.

c) Activation

The composition obtained as described in paragraph b) is placed in a reactor for calcination, which is flushed with air at 130° C. for 4 hours.

The reactor is then brought to 530° C. for 1 hour under air.

The reactor is then cooled under nitrogen to ambient temperature and left to stand overnight under these conditions.

The reactor is then brought to 280° C. under nitrogen and is then flushed with hydrogen for 4 hours at 280° C.

The reactor is then brought back to ambient temperature while flushing with nitrogen.

The specific area and the pore volume of the catalytic composition determined by adsorption of nitrogen are, respectively, 45 m$^2$/g and 0,34 cm$^3$/g.

EXAMPLE 7

Production of Chloroform from Carbon Tetrachloride 10 cm$^3$ (8,24 g) of the catalytic composition obtained as described in Example 6 are introduced as a fixed bed into a stainless steel reactor having an internal diameter of 10.2 mm and heated by means of a pulsed-air oven.

The reactor is fed with a gas mixture consisting of 83.3% by volume of hydrogen and 16.7% by volume of carbon tetrachloride at a temperature of 90° C. under a pressure of 4.0 bar and at a space velocity (that is to say the inverse of the average contact time) of 514 h$^{-1}$, which corresponds to a hydrogen flow rate of 12.9 1N/h and a carbon tetrachloride flow rate of 2.6 1N/h.

The initial degree of conversion of carbon tetrachloride is 98 mol %.

The products formed are chloroform, dichloromethane, hydrochloric acid and traces of ethane and perchloroethylene. The selectivities, based on carbon tetrachloride converted, are, respectively, 80 mol % for chloroform, 2 mol % for dichloromethane and 18 mol % for methane.

EXAMPLE 8

Production of Chloroform from Carbon Tetrachloride—Dilution of the Carbon Tetrachloride with Hydrogen or Hydrogen and Methane After the reactor containing the catalytic composition of Example 6 has been in operation for 22 hours under the conditions of Example 7, a gas mixture consisting of 88.9% by volume of hydrogen and 11.1% by volume of carbon tetrachloride is introduced into the reactor at a temperature of 90° C. under a pressure of 4 bar and at a space velocity of 514 h$^{-1}$, which corresponds to hydrogen and carbon tetrachloride flow rates of, respectively, 13.7 1N/h and 1.7 1N/h.

Under these conditions the degree of conversion of carbon tetrachloride is 98 mol %. The selectivities, based on carbon tetrachloride converted, are, respectively, 87 mol % for chloroform, 1 mol % for dichloromethane and 12 mol % for methane.

After a further additional 6 hours of operation, a gas mixture consisting of 44.4% by volume of hydrogen, 44.4 by volume of methane and 11.2% by volume of carbon tetrachloride is introduced into the reactor at a temperature of 100° C. under a pressure of 4 bar and at a space velocity of 514 h$^{-1}$, which corresponds to hydrogen, methane and carbon tetrachloride flow rates of, respectively, 6.7 1N/h, 6.7 1N/h and 1.7 1N/h.

Under these conditions the degree of conversion of carbon tetrachloride is 98 mol %. The selectivities, based on carbon tetrachloride converted, are, respectively, 86 mol % for chloroform, 1 mol % for dichloromethane and 13 mol % for methane.

We claim:

1. A process for the production of chloroform from carbon tetrachloride, in the gas phase in the presence of molecular hydrogen, comprising dechlorinating carbon tetrachloride in the presence of a catalytic composition comprising at least one hydrogenation catalyst deposited on a support comprising at least one alkali metal aluminate or alkaline earth metal aluminate.

2. The process according to claim 1 wherein the support comprises at least one aluminate having an inverse spinel structure.

3. The process according to claim 2 wherein the aluminate used comprises a lithium aluminate of formula $LiAl_5O_8$.

4. The process according to claim 1 wherein the support comprises a mixed aluminate of at least two metals selected from the alkali metals and the alkaline earth metals.

5. The process according to claim 1 wherein the support comprises a mixture of at least two different aluminates of metals selected from the alkali metals and the alkaline earth metals.

6. The process according to claim 1 wherein the molar ratio between hydrogen and carbon tetrachloride is between 1 and 16.

7. The process according to claim 1 wherein the gas phase is diluted with methane.

8. The process according to claim 1 wherein the temperature at which the reaction takes place is between 50° and 200° C.

9. The process according to claim 1 wherein said hydrogenation catalyst is selected from the metals of Group VIII and Group IB of the Periodic Table of the Elements.

10. The process according to claim 1 wherein said hydrogenation catalyst is selected from the group consisting of Ru, Rh, Pd, Os, Ir, Pt, Cu, Ag and Au.

11. The process according to claim 1 wherein said hydrogenation catalyst is selected from the group consisting of platinum and palladium.

12. The process according to claim 11, wherein said hydrogenation catalyst is platinum.

13. The process according to claim 1, wherein said support is selected from the group consisting of lithium aluminate, magnesium aluminate and calcium aluminate.

14. The process according to claim 3, wherein said support comprises at least 75% of lithium aluminate of formula $LiAl_5O_8$.

15. The process according to claim 1, wherein said support comprises lithium aluminate of formula $LiAl_5O_8$ and lithium oxide of the formula $LiAlO_2$.

* * * * *